(12) United States Patent
Cheetham

(10) Patent No.: US 9,775,690 B2
(45) Date of Patent: Oct. 3, 2017

(54) MIXING AND DISPENSING CONTAINER

(71) Applicant: Joshua James Cheetham, Bensenville, IL (US)

(72) Inventor: Joshua James Cheetham, Bensenville, IL (US)

(73) Assignee: SDI NORTH AMERICA INC., Bensenville, IL (US)

( * ) Notice: Subject to any disclaimer, the term of this patent is extended or adjusted under 35 U.S.C. 154(b) by 0 days.

(21) Appl. No.: 13/956,323

(22) Filed: Jul. 31, 2013

(65) Prior Publication Data

US 2014/0034670 A1    Feb. 6, 2014

(30) Foreign Application Priority Data

Aug. 1, 2012 (AU) ................... 2012903298

(51) Int. Cl.
*A61C 5/64* (2017.01)
*B05C 17/005* (2006.01)
*B65D 25/08* (2006.01)
*B65D 47/30* (2006.01)
*A61C 9/00* (2006.01)
(Continued)

(52) U.S. Cl.
CPC .............. *A61C 9/0026* (2013.01); *A61C 5/64* (2017.02); *B05C 17/00553* (2013.01); *B05C 17/0106* (2013.01); *B65D 25/08* (2013.01); *B65D 47/10* (2013.01); *B65D 47/103* (2013.01); *B65D 47/106* (2013.01); *B65D 81/3222* (2013.01); *B65D 83/0005* (2013.01); *B65D 83/687* (2013.01)

(58) Field of Classification Search
CPC .......... B05C 17/0106; B05C 17/00553; B65D 83/687; B65D 83/0005; B65D 81/3222; B65D 47/10; B65D 47/103; B65D 47/106; B65D 25/08; B29B 7/7663; A61C 5/64; A61C 9/0026
USPC ..... 222/80–82, 129, 145.1, 145.5, 326, 386, 222/135–136, 541.1–541.4
See application file for complete search history.

(56) References Cited

U.S. PATENT DOCUMENTS 2,665,690 A * 1/1954 Lockhart ................... 206/221
2,754,590 A * 7/1956 Cohen ...................... A61C 5/04
                                                         433/90

(Continued)

*Primary Examiner* — Frederick C Nicolas
(74) *Attorney, Agent, or Firm* — William H. Holt

(57) ABSTRACT

A container 10 for mixing and dispensing of material having a liquid receptacle 14 and a plunger 18. The receptacle 14 has a front portion 36 and the plunger 18 has a forwardly projecting sharp protrusion 42 having a shaft 72 which terminates in a sharp outer end 78, 82. Upon the plunger 18 being depressed the sharp protrusion 42 pierces a front portion 36 of the liquid receptacle 14 and the liquid in the receptacle 14 is pushed hydraulically through the front portion 36 into a main chamber 17. Thus the liquid contacts material in the main chamber 17 to form a mixture. The plunger 18 can continue to be depressed so as to break the front portion 36 of the liquid receptacle 14 away and then push the material in the main chamber 17 towards a dispensing nozzle 26. The main chamber 17 has a frangible membrane 22 at a distal end 13 thereof which is hydraulically broken by pressure applied from the material in the main chamber 17 so that the material can be dispensed from the container 10. The container 10 is particularly envisaged for use with mixing and dispensing of dental materials.

12 Claims, 4 Drawing Sheets

(51) Int. Cl.
*B65D 47/10* (2006.01)
*B65D 81/32* (2006.01)
*B65D 83/00* (2006.01)
*B05C 17/01* (2006.01)
*B65D 83/68* (2006.01)

(56) References Cited

U.S. PATENT DOCUMENTS

| | | | | |
|---|---|---|---|---|
| 3,028,052 | A * | 4/1962 | Archer | 222/136 |
| 3,756,390 | A * | 9/1973 | Abbey et al. | 206/219 |
| 4,648,532 | A * | 3/1987 | Green | 222/82 |
| 4,941,751 | A * | 7/1990 | Muhlbauer | 366/182.1 |
| 5,026,283 | A * | 6/1991 | Osanai et al. | 433/90 |
| 5,172,807 | A * | 12/1992 | Dragan et al. | 206/219 |
| 6,349,850 | B1 * | 2/2002 | Cheikh | 222/1 |
| 8,443,970 | B2 * | 5/2013 | Coon | B65D 51/2835 206/219 |
| 8,584,838 | B2 * | 11/2013 | Cheetham | 206/219 |
| 8,690,570 | B2 * | 4/2014 | Cheetham | 433/90 |
| 8,893,925 | B2 * | 11/2014 | Cheetham | 222/145.5 |
| 2001/0053511 | A1 * | 12/2001 | Aoyagi et al. | 433/90 |
| 2011/0056984 | A1 * | 3/2011 | Cheetham | 222/135 |

* cited by examiner

MIXING AND DISPENSING CONTAINER

FIELD OF THE INVENTION

The present invention relates to a mixing and dispensing container.

SUMMARY OF THE INVENTION

In accordance with one aspect of the present invention there is provided a container for the mixing and dispensing of material, which comprises a body having a main chamber, a dispensing nozzle, a liquid receptacle and a plunger, wherein the receptacle has an front portion and the plunger has a forwardly projecting sharp protrusion, the plunger being in sealing engagement with the liquid receptacle such that, in use, upon the plunger being depressed the sharp protrusion pierces the front portion of the liquid receptacle and liquid in the receptacle is then pushed hydraulically from the receptacle through the front portion into the main chamber of the body so as to contact material in the main chamber to form a mixture, and wherein subsequently a front portion of the liquid receptacle is arranged to be entirely detached from the remainder of the liquid receptacle by continued depression of the plunger such that the plunger is able to traverse the entire length of the main chamber together with the detached front portion to facilitate dispensation of the mixture from the main chamber into the dispensing nozzle, the remainder of the liquid receptacle remaining stationary throughout.

DESCRIPTION OF THE DRAWINGS

The present invention will now be described, by way of example, with reference to the accompanying drawings, in which.

DETAILED DESCRIPTION OF THE DRAWINGS

Referring to the FIGS. 1 to 5 of the accompanying drawings there is shown a container that is particularly envisaged to be used for dispensing of a dental material, in which a front portion of a liquid receptacle is entirely detached from the liquid receptacle.

Figure 1:
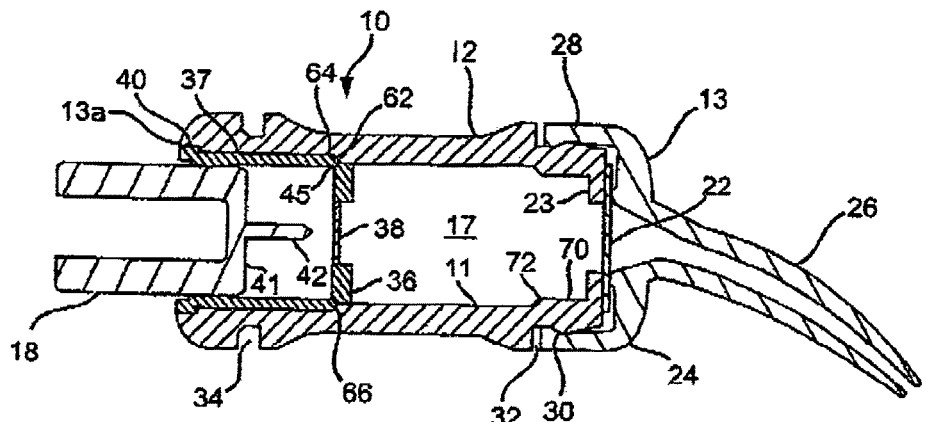
FIG. 1 is a longitudinal sectional view of a container in accordance with the present invention in an initial condition.

Referring to FIG. 1, there is shown a container 10 in an initial open or storage condition. The dental container 10 comprises a body 12 which has an internal surface 11 and is substantially cylindrical in cross section. Inside the body 12 is an open ended liquid receptacle 14, which is arranged to contain a liquid. The receptacle 14 is sealed by a plunger 18 such as by seal means located on an external surface of the plunger 18 or on an internal surface of the liquid receptacle 14.

The plunger 18 is initially located in an open end of the receptacle 14 as shown and has a front face 41. Further, as shown the front face 41 of the plunger 18 has extending therefrom a sharp forwardly projecting protrusion 42.

The body 12 contains a main chamber 17 which is arranged to house an amount of powder. The main chamber of the body 12 is sealed at a distal end 13 by a frangible membrane 22 which is connected to the body 12 such as at an annular inwardly extending flange 23 by any convenient means such as an adhesive. The distal end 13 of the body 12 is opposed to a proximal end 13a thereof. The membrane 22 may be less than 0.01 mm thick. It may also be formed of a single unitary sheet of a plastics material or a multilayer material such as an adhesive/foil membrane material.

The body 12 has attached thereto an end cap 24 which is connected to a nozzle 26 for dispensing material. The cap 24 is connected to the body 12 by means of a circumferential flange 28 which has an inwardly extending annular rib 30 at an end thereof remote from the nozzle 26. The rib 30 engages with a circumferential recess 32 in the body 12.

Further, the body 12 is provided with an outward facing circumferential groove 34 adjacent the plunger 18. The groove 34 is arranged to engage with a dispensing apparatus (not shown) in use.

Still further, the liquid receptacle 14 has a side wall 37 and an inner front portion 36 with a central weakened portion 38. The central weakened portion 38 is substantially thinner than the remainder of the front portion 36 of the liquid receptacle 14. For example the central weakened portion may be a membrane less than 0.01 mm thick. It may also be in the form of a single unitary sheet of plastics material.

A junction between the side wall 37 and the front portion 36 is defined by an angle 45. The front portion 36 is, in the condition shown in FIG. 1, spaced from a front face 41 of the plunger 18. Further, the front face 41 of the plunger 18 is provided with the sharp forwardly extending protrusion 42.

Figure 2:
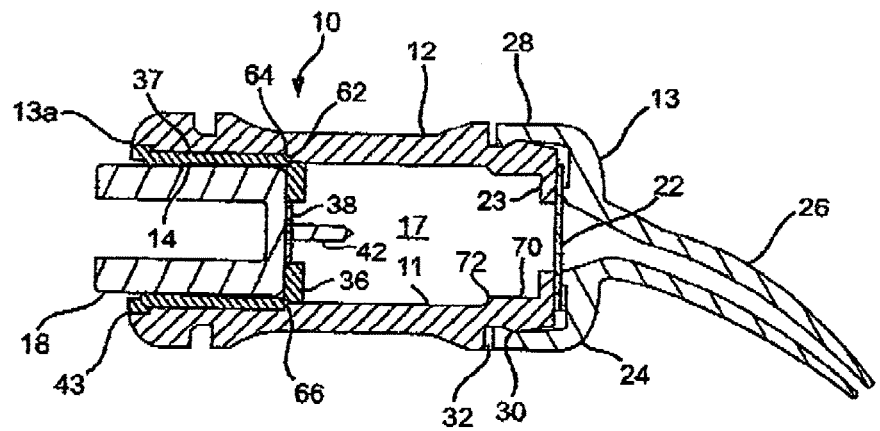
FIG. 2 is a longitudinal sectional view of the container of FIG. 1 in a partially activated condition.

Referring to FIG. 2, there is shown the container 10 in an activated condition. The activated position is achieved through the plunger 18 being depressed. This action causes the plunger 18 to be moved so that initially the sharp protrusion 42 engages with and then pierces the weakened section 38 of the front portion 36. The plunger then moves forward until the front face 41 thereof engages with the front portion 36 and displaces the liquid hydraulically. The liquid is thus forced through a small hole in the weakened section 38 around the protrusion 42 formed by the piercing action into the main chamber 17 of the body 12 by the front face 41. The membrane of the weakened portion 38 remains tightly sealed around the protrusion 42 but is sufficiently flexible to allow the liquid to pass through. This prevents liquid being shaken out of the chamber 17 during mixing. The container 10 may then be placed into a known vibrating mixing device. The liquid and the powder are admixed and thereby form a paste in the chamber 17.

Figure 3:
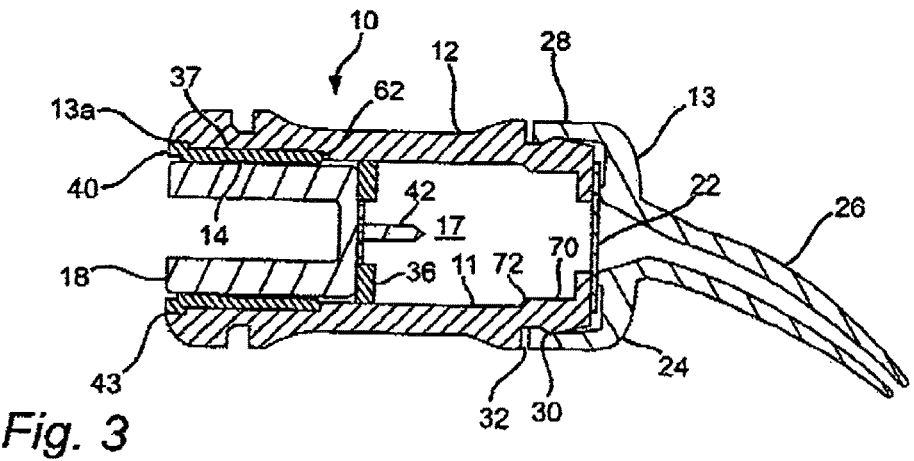
FIG. 3 is a longitudinal sectional view of the container of FIG. 1 in a further partially activated condition.

Referring to FIG. 3, there is shown the container 10 after the plunger 18 has been depressed and the liquid and the powder have been mixed to form a paste. The main chamber 17 of the body 12 now contains the paste. The front portion 36 of the liquid receptacle 14 has broken away from the remainder of the liquid receptacle 14. This is forced by force being transferred from the front face 41 of the plunger 18 to the front portion 36 of the liquid receptacle 14 during dispensing of the paste with a dispensing apparatus. The side wall 37 of the liquid receptacle 14 remains substantially intact. The remainder of the liquid receptacle 14 remains in place by virtue of an outwardly projecting annular step 40 o the liquid receptacle 14 engaging with an annular recess 43 in the inner surface 11 of the body 12.

There is preferably a sharp substantially right angle bend 45 between the front portion 36 and the side wall 37 of the receptacle 14. The bend 45 is preferably devoid of any radius and provides a stress concentration point to facilitate breaking off of the front portion 36. Force placed on the plunger 18 tends to cause a transfer and concentration of energy at the bend 45 leading to separation of the inner portion 36 at the bend 45 as shown in FIG. 3.

Figure 4:
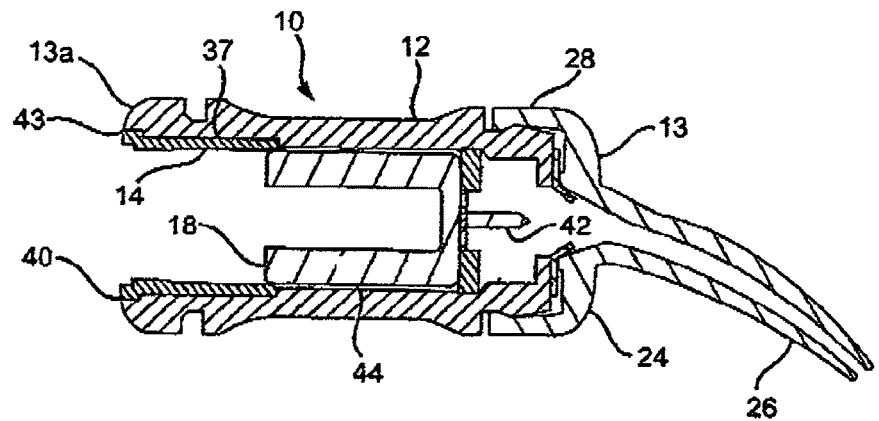
FIG. 4 is a longitudinal sectional view of the container of FIG. 1 in a yet further activated condition.
Figure 6:
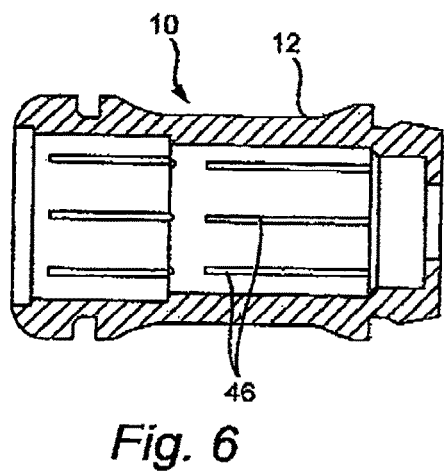
FIG. 6 is a longitudinal sectional view of the container of FIGS. 1 to 5 showing some internal features of the container.

As shown in FIG. 4, the plunger 18 forces the front portion 36 of the liquid receptacle 14 along the main chamber 17, where the front portion 36 of the liquid receptacle 14 acts as a seal and prevents paste from travelling rearwardly. Means such as slots located in the main body internal wall 11 may be provided to act as vent means for entrapped air to escape from the powder. The entrapped air will vent into a recess 44 created from the separation of the front portion 36 of the liquid receptacle 14. The slots may take the form of a plurality of elongated substantially parallel slots 46 which can be seen in FIG. 6 or other forms.

Figure 5:
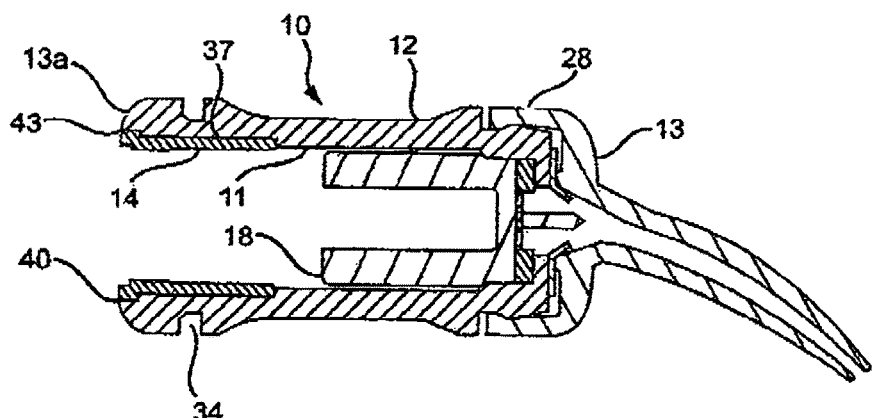
FIG. 5 is a longitudinal sectional view of the container of FIG. 1 in a fully activated condition.

Referring to FIG. 5, there is shown the container 10 once substantially all of the paste has been dispensed. The front portion 36 of the liquid receptacle 14 has been displaced forwardly by the plunger 18 until it approaches the flange 23 of the body 12. As the plunger 18 is displaced forwardly hydraulic pressure on the paste bursts the membrane 22, allowing fluid communication between the main chamber 17 and the nozzle 26 and subsequent dispensing of the paste to a desired location.

Figure 7:
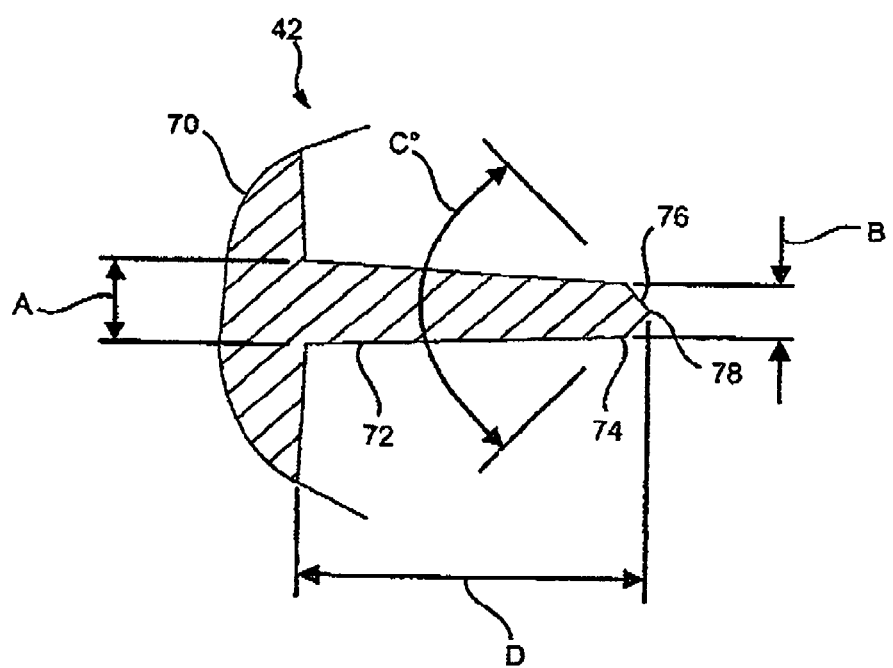
FIG. 7 is a lateral cross sectional view of a sharp protrusion of the container of FIGS. 1 to 6.

Referring to FIG. 7, there is shown a cross section of a preferred embodiment of the sharp protrusion 42 shown in FIGS. 1 to 5.

It can be seen that the protrusion 42 comprises a head 70 for engagement with a rear face of the inner wall 36. A shaft 72 projects longitudinally from the head 70 and extends through the inner wall 36. The shaft 72 at A may be from 3 to 7 mm long preferably about 4 mm. The shaft 72 has a sharp point 74 remote from the head 70.

The shaft 72 may be from 0.3 mm to 2 mm wide at A where it joins the head 70, preferably about 0.7 mm. The shaft may have zero taper but it can taper inwardly preferably in the range from 0.1 to 6 degrees. The shaft 72 preferably has a width from 0.2 mm to 1.6 mm adjacent the point 74 at B. The point 74 has an angled face 76 which has a side wall which terminates at an outer end of the point 74 at a sharp outer end 78 such that the angle C is preferably less than 90°, preferably from 60-70°. Thus, the point 74 may be conical or it may be an oblique cone. The base of the point 74 may be square or any other convenient shape.

Figure 8:
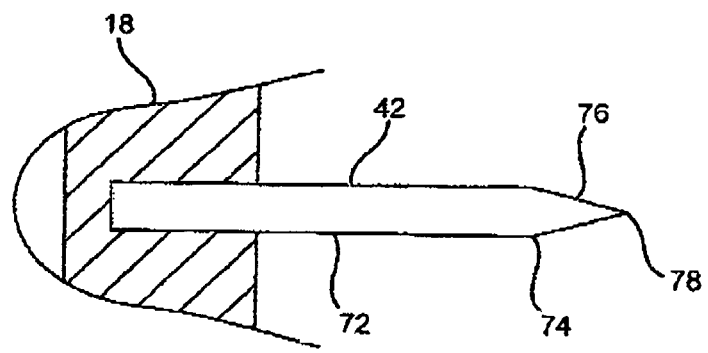
FIG. 8 is a side elevation of a first alternative sharp protrusion.

In FIG. 8 there is shown a first alternative embodiment of sharp protrusion 42 from that shown in FIG. 7 and like reference numerals denote like parts.

In FIG. 8 the sharp protrusion 42 is embedded in the plunger 18 at the time the plunger 18 is produced. The sharp protrusion 42 may be a polymer coated metal pin having an outer taper to produce a sharp point 74 having a sharp outer end 78.

Figure 9:
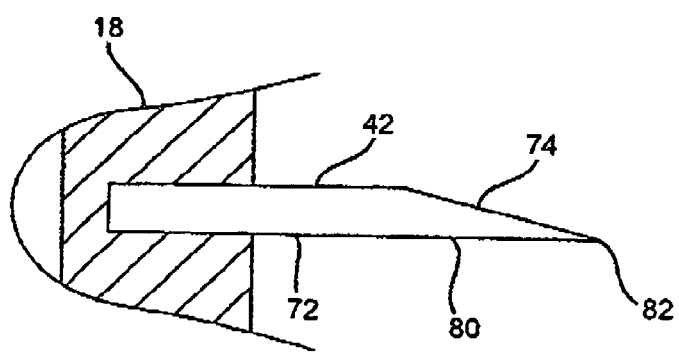
FIG. 9 is a side elevation of a second alternative sharp protrusion

In FIG. 9 there is shown a second alternative embodiment of sharp protrusion 42 from that shown in FIG. 7 and like reference numerals denote like parts. In this embodiment the sharp point 74 is produced by forming a wedge 80 having a sharp outer end 82.

Preferably in the embodiments of FIGS. 8 and 9, the metal pins described have diameters in the range from 0.1 to 0.5 mm preferably about 0.3 mm In use a user holds the container 10 and places the plunger 18 onto a flat surface, such as a table, to transfer application of pressure to the plunger 18. Pressure applied to the plunger 18 causes the plunger 18 to move forward and the protrusion 42 to break through the weakened portion 38. The liquid 16 then enters the main chamber 17. The plunger 18 is then displaced forward again by the dispensing device. This brings the front face 41 of the plunger 18 into close abutting contact with a rear of the front portion 36.

The main chamber 17 now contains the liquid and the powder. The user then places the container 10 in an appropriate mixing device such as a vibration mixer. The agitation caused by the mixing device causes the liquid and the powder to mix and combine to form a paste.

After mixing, further forward displacement of the plunger 18 places increasing pressure against the liquid receptacle 14. Once sufficient force is applied the front portion 36 of the liquid receptacle 14 breaks away as shown in FIGS. 3 and 4. This leaves the side wall 37 of the liquid receptacle 14 substantially intact.

As the plunger 18 is displaced forward slots 46 in the interior surface 11 of the main chamber 17 may allow for any air trapped within the container 10 or mixed material to vent into the recess 44 created from the separation of the front portion 36 of the liquid receptacle 14 from the side wall 37. Further, it is possible that the mixing process does not fully mix all of the powder components and some residual powder is left behind in, for example, the area between the front portion 36 of the liquid receptacle 14 and the internal wall 11 of the body 12. This in practice may cause the dental material to become contaminated by a residual powder component. As the plunger 18 and the front portion 36 move forward the recess 44 is formed behind the front portion 36. Powder particles that have remained unmixed are able to enter the recess 44 hence reducing the risk of contamination or exposure of the user of these particles.

Further forward displacement of the plunger 18 will cause the plunger 18 to travel to the distal end of the body 12 as shown in FIG. 5. This will lead to increased hydraulic pressure against the frangible member 22. Once the hydraulic pressure reaches a critical value the membrane 22 will burst. The paste is thus placed in fluid communication with the nozzle 26. Still further, forward displacement of the plunger 18, as shown in FIG. 5, will cause the paste to travel through the nozzle 26 before finally being dispensed.

In the accompanying drawings there is shown the container 10 has an internal surface 11 with an internal step 62 such that the proximal end 13a of the body 12 is of larger dimension than the distal end 13.

Further the side wall 37 of the receptacle is provided with an open sided annular recess 64 adjacent the inner portion 36.

As can be seen the arrangement of the recess 64 and the step 62 enables the receptacle 14 to have a thin section 66 adjacent the inner portion 36. Thus, when force is applied to the plunger 18 as described hereinabove, the inner portion 36 breaks free of the receptacle 14 as shown in FIG. 3 at the thin section 66. This is because the section 66 is relatively weak compared to the inner portion 36. Also, because the distal end 13 of the chamber 17 is smaller in internal diameter than the proximal end portion 13a, all of the force applied to the plunger 18 is concentrated at the step 62 and the thin section 66. Thus, the inner wall 36 breaks away as described above, in use.

It can also be seen that the main chamber has an optional compression zone 70 adjacent the distal end 13 thereof. The compression zone comprises a step 72. Preferably a proximal face of the step 72 is tapered to provide a smooth transition from the main part of the inner wall 11 and the compression zone 70. The compression zone 70 provides a degree of resistance to the movement of the front portion 36 during extrusion of the material.

Modifications and variations as would be apparent to a skilled addressee are deemed to be within the scope of the present invention.

The invention claimed is:

1. A container for the mixing and dispensing of dental material,
   said container comprising a body with a main chamber having a length,
   a dispensing nozzle,
   a liquid receptacle and a plunger,
   said liquid receptacle having an inner front portion and said plunger being moulded and having a shaft forwardly projecting from said plunger terminating in a sharp outer end,
   said shaft having a portion adjacent to said plunger which is of substantially uniform cross-section throughout and an outer end portion which slopes inwardly towards an outer end of said shaft such that said shaft terminates in a sharp outer end,
   said sharp outer end of said shaft being in the shape of a cone, said inner front portion of said liquid receptacle having a central weakened portion which is substantially wider than said shaft of said plunger,
   said plunger being arranged for linear depression such that said sharp outer end pierces said inner front portion of said liquid receptacle at said central weakened portion wherein continued linear depression of said plunger causes liquid in said liquid receptacle to be pushed hydraulically from said liquid receptacle through said inner front portion around said shaft into said main chamber of said body for contacting material in said main chamber for forming a mixture,
   said inner front portion of said liquid receptacle being circumferentially weakened to be entirely detached from the remainder of said liquid receptacle by continued linear depression of said plunger such that said plunger traverses said length of said main chamber entirely together with said detached inner front portion for facilitating dispensation of said mixture from said main chamber into said dispensing nozzle, said remainder of said liquid receptacle remaining stationary throughout.

2. A container according to claim 1, wherein said weakened portion of said inner front portion of said liquid receptacle is substantially thinner than the remainder of said inner front portion of said liquid receptacle, and in use, said shaft engages with and then pierces said inner front portion in said central weakened portion thereof so that said liquid in said liquid receptacle is pushed hydraulically through said pierced central weakened portion.

3. A container according to claim 2, wherein said detached front portion of said liquid receptacle functions as a seal as it traverses the entire length of said main chamber.

4. A container according to claim 2, wherein said main chamber of said body is sealed at a distal end remote from said liquid receptacle by a separate frangible membrane.

5. A container according to claim 3, wherein said main chamber of said body is sealed at a distal end remote from said liquid receptacle by a separate frangible membrane.

6. A container according to claim 4, wherein said frangible membrane at the distal end of said main chamber is arranged to be broken by hydraulic pressure applied by said detached front portion of said liquid receptacle by said mixed material contained in said main chamber after mixing.

7. A container according to claim 2, wherein said central weakened portion has a thickness of less than 0.01 mm.

8. A container according to claim 2, wherein said central weakened portion is formed of a unitary sheet of material.

9. A container according to claim 7, wherein said central weakened portion is formed of a unitary sheet of material.

10. A container according to claim 4, wherein said frangible membrane has a thickness of less than 0.01 mm.

11. A container according to claim 4, wherein said frangible membrane is formed of a unitary sheet of material.

12. A container according to claim 10, wherein said frangible membrane is formed of a unitary sheet of material.

* * * * *